United States Patent
Ott

(10) Patent No.: US 7,292,340 B2
(45) Date of Patent: Nov. 6, 2007

(54) PROCEDURE FOR DETECTING AND CLASSIFYING IMPURITIES IN LONGITUDINALLY MOVING TEXTILE INSPECTION MATERIAL

(75) Inventor: Philipp Ott, Steg (CH)

(73) Assignee: Uster Technologies AG, Uster (CH)

( * ) Notice: Subject to any disclaimer, the term of this patent is extended or adjusted under 35 U.S.C. 154(b) by 168 days.

(21) Appl. No.: 10/539,204

(22) PCT Filed: Dec. 17, 2003

(86) PCT No.: PCT/CH03/00821

§ 371 (c)(1),
(2), (4) Date: Nov. 18, 2005

(87) PCT Pub. No.: WO2004/063746

PCT Pub. Date: Jul. 29, 2004

(65) Prior Publication Data

US 2006/0230823 A1     Oct. 19, 2006

(30) Foreign Application Priority Data

Jan. 8, 2003    (CH) ................................... 0026/03

(51) Int. Cl.
G01N 21/84    (2006.01)
(52) U.S. Cl. ..................... 356/430; 356/238.2
(58) Field of Classification Search ............. None
See application file for complete search history.

(56) References Cited

U.S. PATENT DOCUMENTS

| | | | |
|---|---|---|---|
| 5,255,561 A | 10/1993 | Fleming et al. | |
| 5,414,520 A | 5/1995 | Joss et al. | |
| 5,430,301 A * | 7/1995 | Shofner et al. | ........... 250/461.1 |
| 5,671,061 A * | 9/1997 | Hoeller | ........................ 356/429 |
| 6,130,746 A * | 10/2000 | Nevel et al. | .............. 356/238.2 |
| 6,912,048 B2 | 6/2005 | Pirani et al. | |
| 6,944,323 B1 | 9/2005 | Pirani et al. | |

FOREIGN PATENT DOCUMENTS

| | | |
|---|---|---|
| EP | 0 277 694 A2 | 8/1988 |
| WO | 01/92875 A1 | 12/2001 |

OTHER PUBLICATIONS

Philipp Ott, U.S. Appl. No. 10/534,247, filed May 10, 2005.

* cited by examiner

Primary Examiner—Michael P. Stafira
(74) Attorney, Agent, or Firm—Buchanan Ingersoll & Rooney PC

(57) ABSTRACT

The invention relates to a method for detecting and classifying foreign material in an inspection lot of textile fibers that is moved lengthwise. The aim of the invention is to allow for the simultaneous inspection of the inspection lot with regard to a plurality of properties and to allow for the detection of a foreign material and for its classification in a simple manner while taking due consideration of all properties measured. According to the invention, values for deviations of these properties from a standard are detected and stored for at least two properties that are influenced by the foreign material. The values for the deviations are eliminated according to a predetermined rule except for the values of one property. A value for the deviation and a value for the length of the deviation on the inspection lot resulting from the values of the remaining property is detected and the foreign material is classified according to this deviation and length.

8 Claims, 4 Drawing Sheets

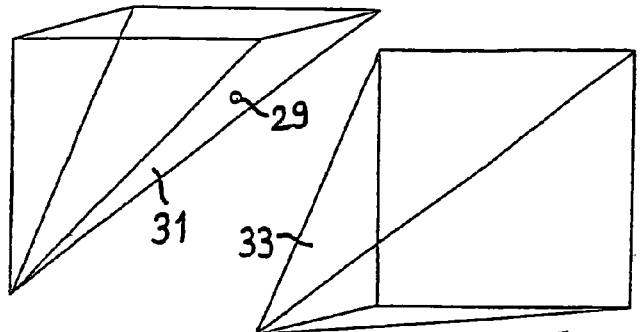
Fig. 5
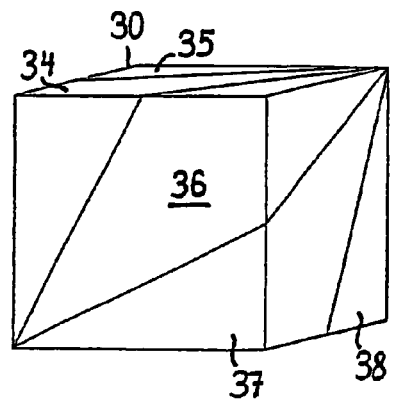
Fig. 6
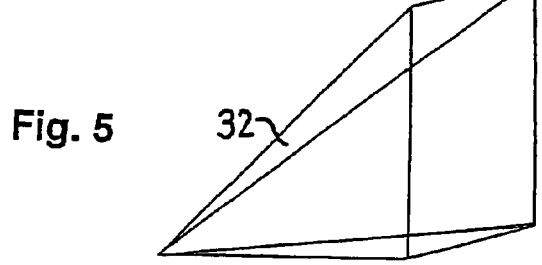
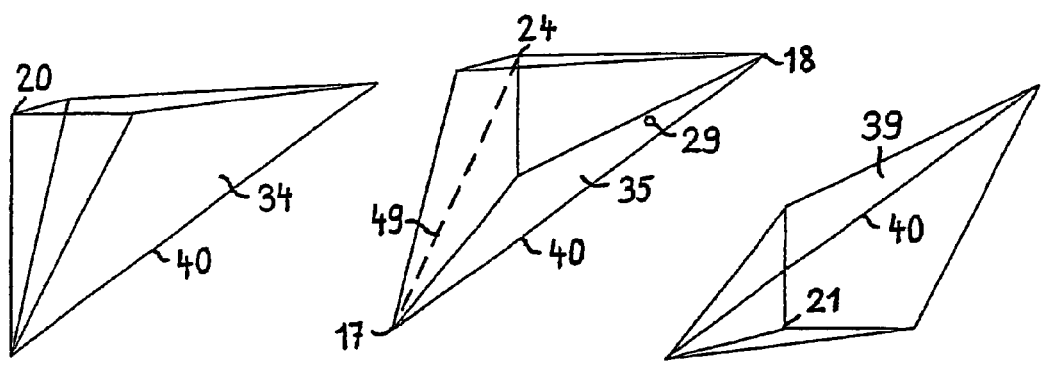
Fig. 7
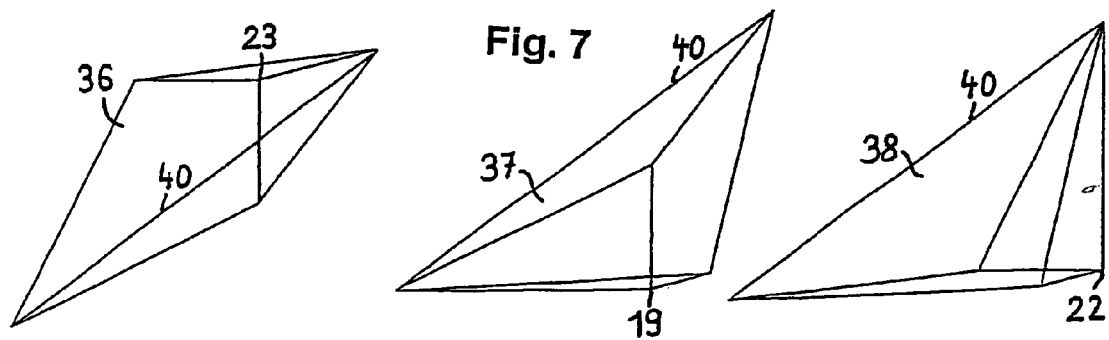

PROCEDURE FOR DETECTING AND CLASSIFYING IMPURITIES IN LONGITUDINALLY MOVING TEXTILE INSPECTION MATERIAL

BACKGROUND OF THE INVENTION

The invention relates to a procedure for detecting and classifying impurities in longitudinally moving inspection material of textile fibres.

Such impurities are to be understood to be, in particular, fibres having other properties, for example, having a colour other than that to be attributed to the basic material. They are also to be understood to include, however, impurities which generally interfere with the normal arrangement of the fibres of the basic material, are not of fibrous constitution, or even constitute actual foreign bodies.

Such a procedure is known from WO 01/92875. In that case, two different properties of the inspection material, such as the capacitance variation in an electric field and the reflection of light by the inspection material, are to be continuously measured. Deviations of measurement values of these properties from a standard value are measured and stored in memory, and can be recorded in a coordinate system in which values for coordinates, which represent both properties, are entered. Through the predefinition of appropriate threshold values or limits for both properties, impurities of a first type can be distinguished from impurities of a second type, and also be selectively subjected to different subsequent processing. In this case, the signals for both properties are each separately compared with their own assessment specifications. The continuous evaluation enables, for example, impurities of a vegetable nature to be distinguished from impurities of a non-vegetable nature, and to be eliminated from the inspection material in a selective and differentiated manner.

A disadvantage of this known procedure is that, in particular, although it is very suitable for distinguishing certain impurities from one another, out of a greater selection of possible impurities it can at best be used for identifying one impurity or an entire group of impurities, without distinguishing between them.

SUMMARY OF THE INVENTION

The invention, as characterized in the claims, therefore achieves the object of creating a procedure which provides for the simultaneous inspection of an inspection material with regard to a plurality of properties, and for the detection of an impurity and for its classification in a simple manner while taking account of all properties measured.

This is achieved in that, for at least two properties that are influenced by impurities, values for deviations of these properties from a respective standard value are measured and stored in memory, the values for the deviations are eliminated according to a predefined rule except for the values of one property, a value for the deviation, resulting from values of the remaining property, and a value for the length of the deviation on the inspection material are ascertained, and the impurity is classified according to this deviation and length. Preferably, a combined value is first to be ascertained from the values for the deviations of the properties and, for the combined value, domains are to be predefined in which such values may be located, wherein determination of values of which property are to be eliminated is effected on the basis of a domain in which the combined value is located. In order to measure values for the properties, the inspection material may, for example, be illuminated with light having a plurality of colours. The reflection of the light is to be measured separately for each colour, and measured values compared with standard values and stored in memory as deviations. The deviations may be conceived as vectors in a space. A total vector is obtained, as a combined value, from the deviations, and domains are predefined for the end-point of the total vector in the space. Depending on the domain in which the end-point is located, at least one first vector is eliminated, with the result that a total vector is obtained in a plane in which there is located at least one residual vector. Its position in this plane is ascertained and, on the basis of the ascertained position, a possibly present further vector is eliminated with the result that there is ascertained, in respect of the value of the remaining vector, an intensity which, together with the value for the length on the inspection material, is used for classification. The impurities are to be classified in a coordinate system which has a first axis for values of the length of the deviation and a second axis for values for the magnitude of the deviation. The second axis may be divided into a plurality of sections for values for different properties.

The advantages achieved by the invention are that it provides for a classification of impurities in, for example, a yarn, that no longer has the limitations of current procedures. It thereby becomes possible to identify impurities in a yarn according to the type of material, and to eliminate them in a selective manner.

BRIEF DESCRIPTION OF THE DRAWINGS

The invention is explained more fully in the following with reference to an example and the accompanying figures, wherein:

FIGS. 4, 5, 6 and 7 show representations of domains for measurement values.

DETAILED DESCRIPTION OF THE PREFERRED EMBODIMENTS

Taking as a basis that, in order to detect and classify impurities in a longitudinally moving inspection material of textile fibres, e.g. in a yarn, the inspection material is separately illuminated with light in a plurality of colours, it is then possible to measure the light reflected on the inspection material. Illumination in this manner has already been described in the patent application CH 2002 1901/02. Measurement values for the reflection are thus obtained, with a mean value or standard value being obtained where no impurity is present. If impurities are present, the measurement values for reflection may deviate from the standard value according to the colour.

Figure 1:
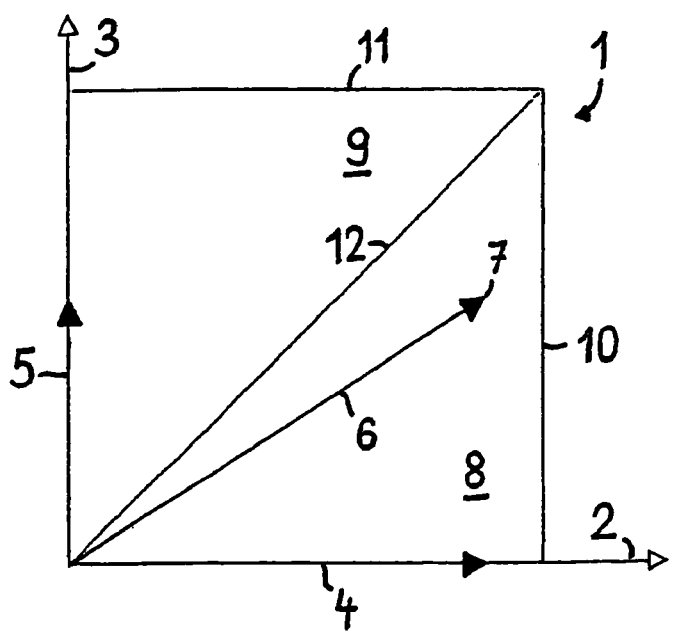
FIG. 1 shows a schematic representation of values measured on the inspection material.

FIG. 1 shows how measurement values, which are measured on a longitudinally moving inspection fabric of textile fibres such as, for example, a yarn, roving or sliver, and which deviate from a standard value, relate to one another and can also be represented. These values, each of which represents a property of the inspection material, in this case, for example, the reflection of light of a respective certain colour, can be represented as vectors in a rectangular coordinate system 1. The latter is formed by two axes 2, 3, each of which is provided for the values of the reflection of light of one colour. Thus, deviations of the reflection for a first colour are represented along the axis 2 by a vector 4, and deviations of the reflection for a second colour are represented along the axis 3 by a vector 5. A combined value or a total vector 6 can be calculated, in known manner, from the vectors 4 and 5. For the end-point 7 of this total vector 6, it is possible to predefine, for example, domains 8 and 9 which are outwardly delimited by axes 2, 3 and also by lines 10 and 11. These lines 10, 11 correspond to maximum values, e.g. 100% for the length of the vectors 4, 5 or for the values represented thereby. A diagonal 12 divides the two domains 8 and 9.

Figure 2:
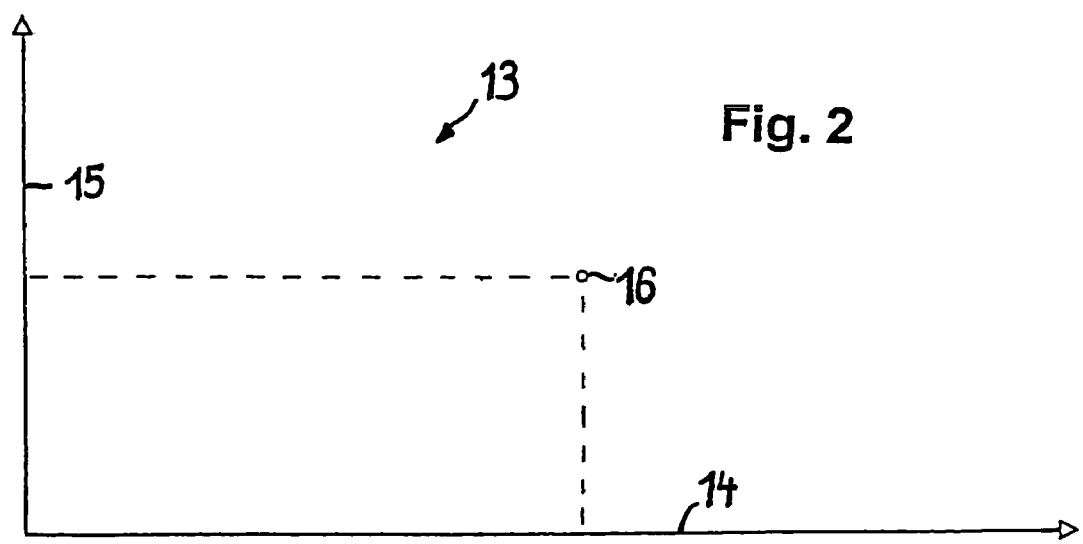
FIG. 2 shows a possible representation for measured properties.

FIG. 2 shows a coordinate system 13 in which deviations of a property of the inspection material can be represented in comparison with a standard value together with the length of the inspection material over which a deviation extends. Thus, for example, values for the length of the deviation are entered along a horizontal axis 14, and values for the magnitude of the deviation from the standard value are entered along a vertical axis 15. In this case, for example, the axis 14 can be conceived as a standard value for a property of the inspection material. In this case, a point 16 above the axis 14 represents a value for a property and for the length of this property on the inspection material.

Figure 3:
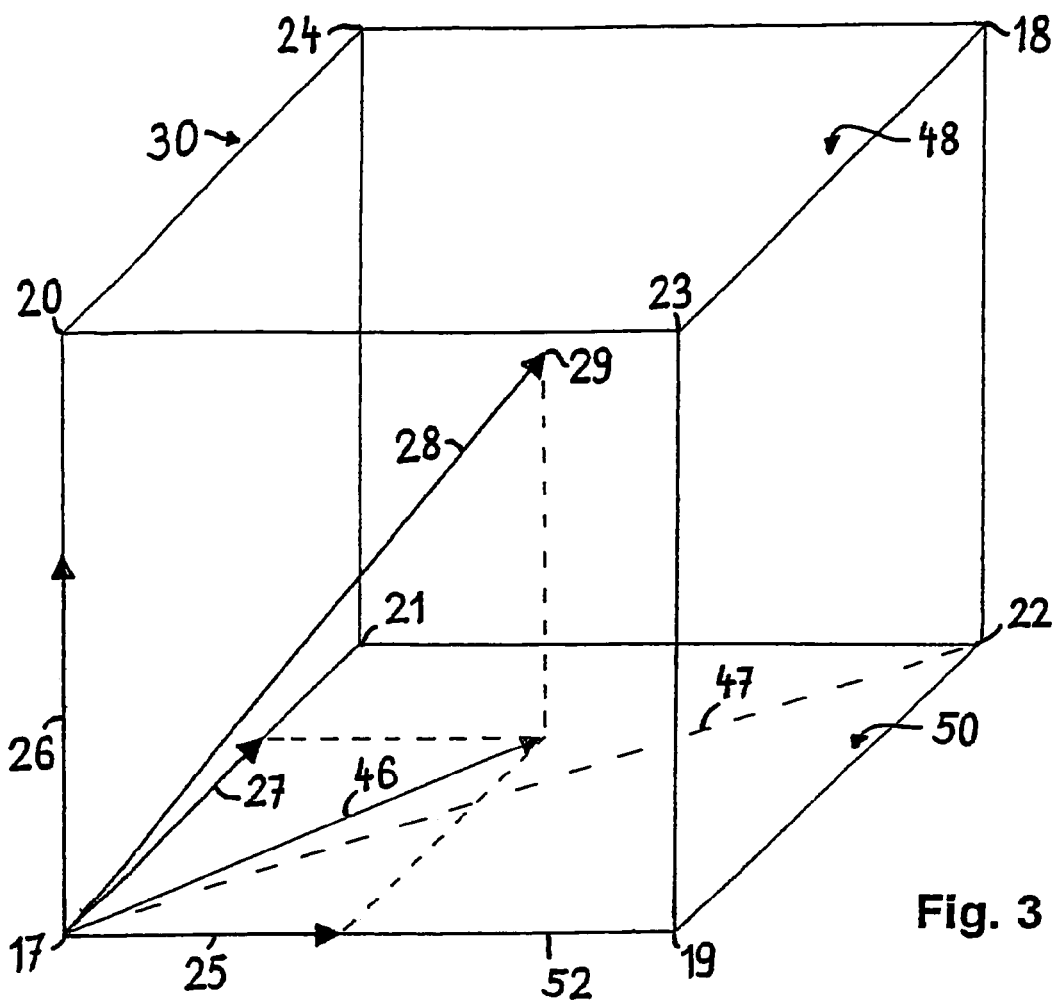
FIG. 3 shows a possibility for the representation of the processing of further measurement values.

FIG. 3 shows a representation corresponding to FIG. 2, but for three different properties of the inspection material. Thus, accordingly, a three-dimensional representation is obtained for three properties in a space which, in this case, is represented as a cube 30. Here again, the reflection of light having three different colours on the inspection material can be predefined as properties. Depending on the basic colour of the inspection material, in most cases a black or a white inspection material will be taken as the basis, so that the reflection of light on the black or white inspection material can be accepted as a standard value. In this FIG. 3, for example, a standard value for the reflection on black-coloured inspection material is to be located in a corner 17, or in a corner 18 for reflection on a white colour. Accordingly, colours can likewise to assigned to the other corners, for example, red to a corner 19, blue to a corner 20, green to a corner 21, yellow to a corner 22, magenta to a corner 23 and cyan or turquoise to a corner 24. Here, vectors 25, 26 and 27 respectively represent a measurement value on the inspection material for the deviation of the reflection of red, blue and green light from a standard value. A total vector 28, having an end-point 29, can be calculated from these vectors 25, 26, 27.

Figure 4:
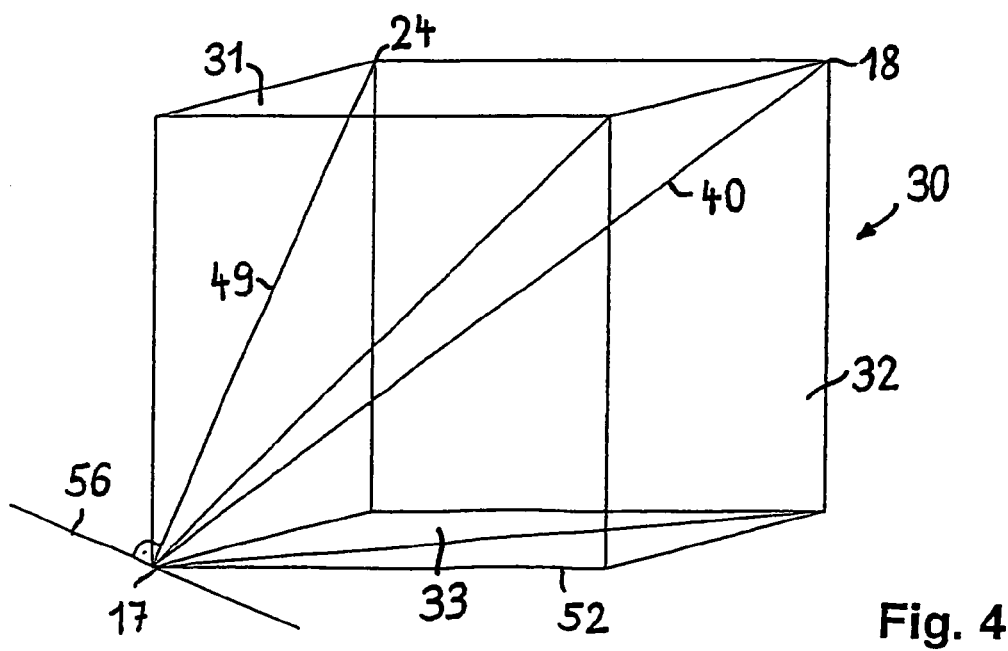

In order to evaluate the total vector 28, the space, as represented by the cube 30 in FIG. 3, is to be divided into domains, as shown, for example, by FIG. 4. Here, the cube from FIG. 3 is shown in reduced scale. The cube 30 in this case is divided into three domains 31, 32 and 33, all of which have in common a diagonal 40 between corners 17 and 18 of the cube 30.

For greater clarity, these three domains 31, 32, 33 are represented again, separately, in FIG. 5, in such a way that, when they are placed together again, they reconstitute the cube 30.

It is of course also possible for the space or cube 30 to be represented with divisions other than those of FIGS. 4 and 5. For example, as shown in FIG. 6, the cube 30 is divided into six domains 34, 35, 36, 37, 38 and 39. In FIG. 7, the domains 34-39 are shown again, separately. When placed together again, they reconstitute the cube 30. A diagonal 40 of the cube 30 adjoins each domain 34-39.

Figure 8:
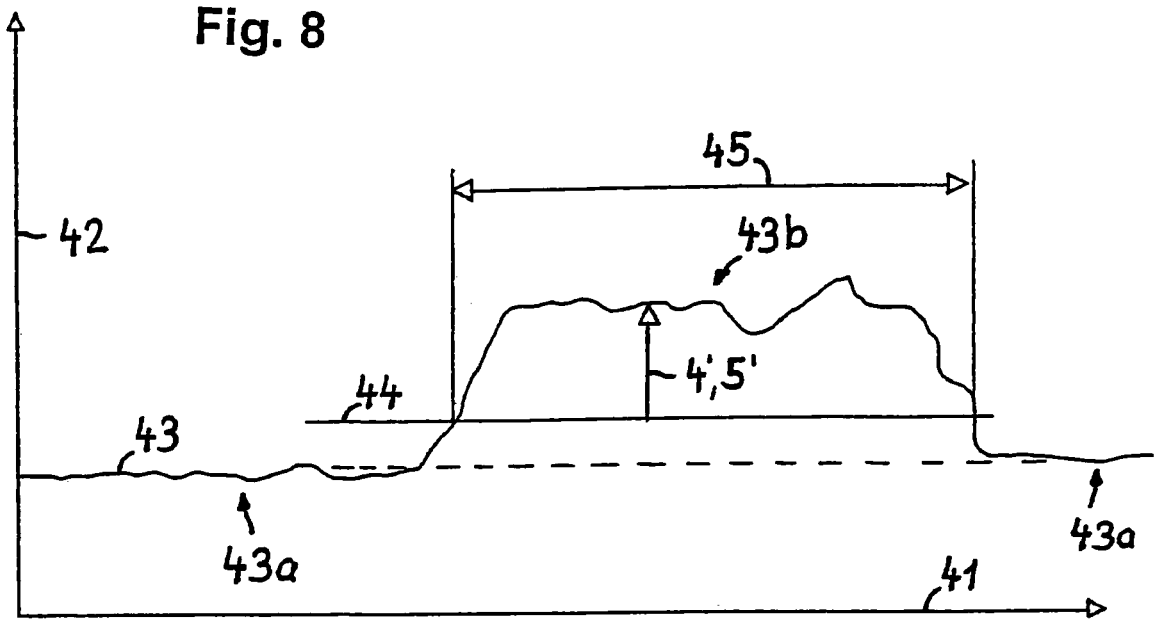
FIG. 8 shows a representation of a typical signal course.

FIG. 8 shows a signal course such as that which can occur in the detection of impurities in a longitudinally moving inspection material. Taking as a basis that values for the length of the inspection material can be entered along an axis 41, and values of, for example, an electrical signal 43 can be entered along an axis 42, a sensor emits a signal 43.

Figure 9:
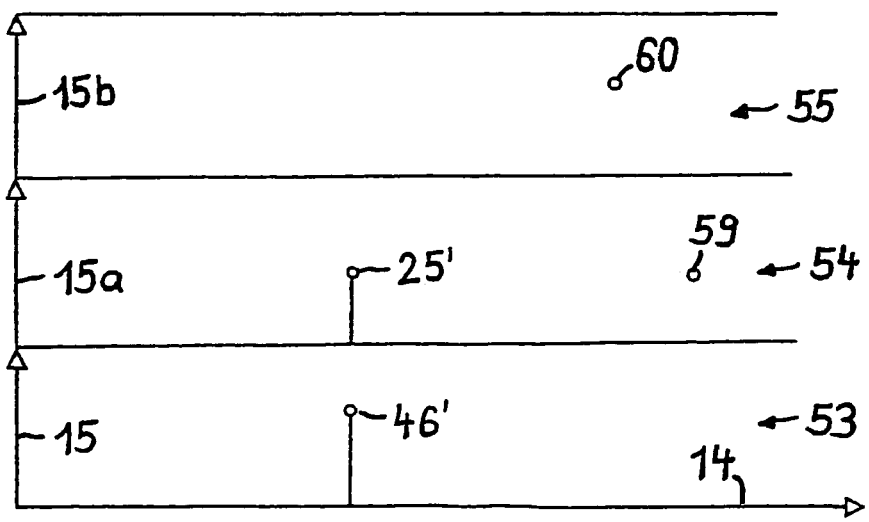
FIG. 9 shows a further possible representation for measured properties.

FIG. 9 combines a plurality of representations, such as those shown in FIG. 2, for a plurality of properties. If colours are provided as properties, then domains 53, 54, 55 are obtained, for example, for the colours blue, green and red. This representation corresponds to three representations according to FIG. 2 arranged one above the other and over the common axis 14. Three axes 15, 15a and 15b are thus also arranged one above the other. Obviously, such an arrangement can be optionally extended for an optional number of properties.

The operating principle of the invention is as follows. If an inspection material is inspected in a sensor that, for example, operates optically and is known from the patent application CH 2002 1901/02, the sensor illuminating the inspection material with light and detecting the light reflected on the inspection material, a signal 43 (FIG. 8) is obtained, which results from the reflected light being converted into an electrical quantity, e.g. a voltage or a current. For normal, uncontaminated inspection material one thus obtains a signal portion 43a which quantifies the reflection of light on the basic colour or on the basic material of the inspection material. This signal portion 43a can be designated as a standard value. The emitted light is preferably of a certain colour. Thus, it is taken as a basis that the capability of the inspection material to reflect light of a certain colour is a property of the inspection material. Accordingly, various other properties are obtained when light of a different colour is to be reflected. It may then be the case that the inspection material contains an impurity, e.g. a fibre of a different colour, a foreign body, etc. It may then likewise be the case that light of a given colour is reflected differently by this impurity than by the basic colour of the basic material of the inspection material. In the example according to FIG. 8, it is taken as a basis that an impurity in the inspection material intensifies the reflection of light, resulting in a signal portion 43b, which produces a signal having a higher value, or excursion. It is also important to ascertain, in this case, the length of the inspection material over which an impurity extends, this being determined by measuring the length of the signal portion 43b. For this, it is expedient first to predefine a threshold value 44 which is located above the signal noise normally expected in the standard-value range. Thus, a length 45 is measured, over which the signal 43 is seen to be continuously over the threshold value 44. This gives the length over which an impurity in the inspection material extends. The same procedure can be achieved with an inspection material with which the reflection of light is reduced. In this way, for an inspection material that contains or might contain impurities, it is possible to measure one or more properties that are influenced by impurities. Such properties are to be understood to include, for example, the capability to reflect light of different colours, to influence electrical or magnetic fields with different characteristics, to influence ultrasound waves, etc.

In order to describe the further processing of the signal 43 as known from FIG. 8, it is taken as a basis that this signal is sampled at a fixed frequency and represented as a vector that varies with time. In this case, the representation as a vector is selected primarily in order that the processing may be better explained. It is obvious, however, that a comparable processing can be achieved through purely computational processing of the signals without vector representation.

According to the present invention, at least two properties are to be measured on an inspection material, using measurement values. This means that, following the measurement on the inspection material, which measurement is known per se and is therefore not described further here, two signals, such as the signal 43, are obtained. To give a concrete example, it could be taken as a basis that one signal is produced by illuminating the inspection material with red light, and the other signal is produced by illuminating it with blue light. It is to be assumed that, over large extents, these signals exhibit a standard value 43*a*, which can be different for both signals and from time to time is replaced by deviations or signal sections 43*b* of a different length.

The further processing of the two signals 43 is now to be described with reference to FIG. 1. The standard values of both signals are not actually of interest. What are of interest, on the other hand, are the deviations or signal portions 43*b* and, particularly in this case, that proportion of the deviations that is located above the threshold value 44. From these deviations there are obtained vectors 4 and 5 in FIG. 1, which are proportional to the length of arrows 4', 5' in FIG. 8. These arrows 4', 5' show how the vectors 4, 5 are derived. In our concrete example, the length of the vector 4 thus indicates the intensity of a property, in this case the intensity with which the red-coloured light is reflected on the inspection material. Accordingly, the length of the vector 5 thus indicates the intensity of a further property, in this case the intensity with which the blue-coloured light is reflected on the inspection material. The values or the vectors are continuously stored in memory for a certain period of time, for further processing. The values or the vectors are then combined with one another, so as to produce a single, combined value. This can be effected according to known rules of vector addition, resulting in a total vector 6 having an end-point 7. Here, the vectors 4, 5 and 6 are represented in a field or space having limits which simultaneously denote maximum values (100%) and minimum values (0%). The limits are constituted by the axes 2 and 3 for minimum values, and by the lines 10 and 11 for maximum values. In addition, for example, the diagonal 12 divides the field into two domains 8 and 9. These domains 8, 9 are then used to ascertain, through a comparison, where the end-point 7 of the total vector is located. This fact is used to apply a predefined rule in order to eliminate values that are derived from the one property, so that it is then only necessary to take account of the values of the other property for further processing of the values. The aim is to indicate, in the representation according to FIG. 2, only a single property and the length on the inspection material over which this property extends. If the properties represented by the vectors 4 and 5 are colours such as red and blue, the combination of both colours, at maximum intensity of each colour, results in a third colour, in this case magenta. This third property or colour then constitutes a reference against which the two properties in question, in this case colours, are to be measured. It is then generally ascertained that this third property or colour is significantly influenced by the one predominant property or colour, which in this case is red, and that the intensity of this third property or the brightness of this third colour is ascertained from the proportion of the reference possessed by the other property or colour, in this case blue. With regard to the situation in FIG. 1, the rule described above indicates that the values, or the vector, to be eliminated are those which result in the end-point being located in the domain which adjoins this vector. Thus, if the end-point 7 of the total vector 6 is located in the domain 8, values of the vector 4 are to be eliminated since, due to the greater length of the vector 4, the latter determines that the end-point 7 is located in the domain 8. If the end-point 7 of the total vector 6 were located in the domain 9, values of the vector 5 would be eliminated. According to this rule, the vectors are thus weighed against one another. The vector that predominates in this comparison is eliminated. In our example, therefore, processing only proceeds with the values of the vector 5 which, in this case, for example, indicates the intensity of the reflection of blue-coloured light on the inspection material. The length of the vector 5 is then transferred as a value into the representation according to FIG. 2 which, together with the length 45 measured according to FIG. 8, results in the point 16. This then means that, of a certain impurity, present in the inspection material, which reflects red light more strongly and blue light less strongly, only the blue light is used for classification according to FIG. 2. It would also be possible to save the elimination of the one value and to classify both properties, but technically this would not provide any further important information about the impurity and would only provide more unused data.

According to the invention, it is also possible to measure three different properties on an inspection material, such as, for example, the capability to reflect light having three different colours. Here, likewise, one might wish to perform a classification, as a result, in such a way that only a single value need be taken into account or represented, in addition to the length over which the property occurs in the inspection material. This is again effected through appropriate elimination of values which denote properties. For this, one takes as a basis measurement values such as those represented, for example, in FIG. 8, but which exist in three different data sets. Thus, again, for each property there is a standard value 43*a* and signal portions 43*b* which denote a deviation, which can be represented by vectors 25, 26 and 27, as shown by FIG. 3.

If, for properties, one takes as an example certain colours, it is then a matter of indicating the result of the measurement values for the colours in respect of their relation to reference colours black and white. The diagonal 40 joins these two reference colours and, consequently, the points 17 and 18. Along this diagonal, and also immediately around it, the colour grey occurs in various graduations between black and white.

For the purpose of classifying impurities, however, more information can be obtained by ascertaining the extent to which they reflect which colours, since colours bear a close relationship to the nature of the impurities. Thus, one could first simply represent the three signals for each colour component. This, however, would introduce too many parameters into the classification and render the latter unclear. According to the invention, therefore, in addition to the said length only one further value is to be indicated, namely, the intensity or brightness between extreme values for one colour out of, for example, three colours.

Taking as a basis that the classification of the impurities is to be effected in relation to three colours, such as red, blue and green, the measured values are represented by the vectors 25, 26 and 27. For the latter it is the case that values of 0 ultimately correspond to the corner 17 in the cube 30, and values of 100% correspond to corners 19, 20 and 21. Here, it is also the case from colour theory that white is obtained as a colour if all three vectors 25, 26 and 27 each result in 100%, and there is thus a mixture of the colours red, blue and green.

If it is further taken as a basis that a total vector 28 having an end-point 29 is calculated from these vectors 25-27, its position is now to be evaluated using three selected domains 31, 32 and 33. Each of the three domains then represents a main colour domain, which means that, out of all known colours of the spectrum, a main colour, and consequently a corner of the cube 30, is assigned to each domain. The three domains 31, 32, 33 all have in common the corners 17 and 18, and a diagonal 40, which joins these two corners 17 and 18.

A rule is now to be applied to determine the values of which property or colour that must be eliminated first. Here, the end-point 29 is located in the domain 31, which is assigned to the main colour blue and therefore to the corner 20. This also means that, in the representation according to FIG. 2, impurities which reflect blue light most strongly are to be classified, by entering values for their brightness and values for their length on the yarn. This brightness, however, is due precisely to the components of the other colours. It is therefore only possible to eliminate those values which constitute the vector 26. This can also be explained by the aforementioned rule, that the length of the vector 26 is predominantly responsible for the fact that the end-point 29 of the total vector 28 comes to be located in the domain 31 (FIGS. 4, 5). Since the colour blue is of no further interest for further considerations, one then continues to consider only the two remaining vectors 25 and 27 and, consequently, the situation in the plane 50 of the cube 30. According to another approach, the plane 50 is also determined in such a way that a plane of projection is sought for the vectors which is perpendicular to the link between the colour black and the colour in question, in this case blue. If this plane of projection is established, a total vector 46, consisting only of the vectors 25 and 27, can be of further assistance in this case. The absolute value of the total vector 46 compared with the absolute value or the length of the diagonal 47 in this case gives the sought value for the brightness, and is to be entered over the axis 14 in FIG. 2 or 9. One may merely add here for explanation that the cube 30 is reduced by a dimension as soon as the first vector is eliminated. Further consideration is thus now limited to one of the two end faces 48 or 50 of the cube 30, and thus to the vectors 25 and 27, as discussed.

It is also possible to use three measured properties to refine the evaluation of the total vector 28, with its end-point 29, ascertained from these three properties, by dividing the cube 30 into, for example, six domains 33-39. Again, this is to be shown for the measurement of properties on the inspection material which are to be measured through the illumination of the inspection material with light in three different colours, being red, blue and green. The division of the cube 30 into six domains 33-39 is shown in FIG. 6. Taking as a basis, as described above, that a colour, including black and white, can be assigned to each corner 17-24 of the cube 30, each domain 33-39 then represents mainly one colour, other than black and white, since each domain 33-39 adjoins one of the corners 19-24. It is then a matter of using these domains to ascertain which values, or which vector, are the first to have no further role in further calculation, and are therefore to be eliminated. Since the situation is significantly less clear in this case, one employs the following procedure which, likewise, can be generally applicable as a rule for the elimination of values in such a space. The domain 33-39 in which the end-point 29 of the total vector 28 is located is ascertained. In this case, it is the domain 35 (FIG. 7). This domain 35 is assigned to the corner 24 which represents the colour cyan or turquoise. This colour is no longer a pure colour, being composed of the colours blue and green, which means that both vectors 26 and 27, added together, represent the proportion of the colour cyan. Thus, only the vector 25 remains responsible for the magnitude of the brightness or the intensity of the colour cyan. The same result is obtained if one asks which vector, or which of the three vectors 25, 26 and 27 contribute to the total vector towards the corner 24 or lead into the domain 35. One immediately identifies that this can only be the vectors 26 and 27, since the vector 25 cannot contribute towards this. In order to evaluate the contribution of this vector 25, one again seeks in the cube 30 a plane of projection which, according to the rule, is perpendicular to a straight joining line between the respective colour (cyan) and black, i.e., perpendicular to a diagonal 49 (FIGS. 4 and 7) between corners 17 and 24. As shown in FIG. 4, such a plane of projection is formed by a line 56 and the cube edge 52. The vector 25, however, is thus located exactly in this plane of projection. Our cube 30 is thus reduced by two dimensions, and there remains one cube edge 52 whose length defines a maximum value for the vector 25. The length of the vector 25 is thus to be related to the length of such a cube edge 52, and the value is obtained which can be entered over the axis 14 in the representation according to FIG. 2 or 9. FIG. 9, depending on the selected division of the cube 30 into three or six domains, then shows two values for the classification of the respective impurity. One value is ascertained by dividing the cube 30 into three domains 31-33, and corresponds to the ratio of the lengths of the total vector 46 and of the diagonal 47. It is therefore denoted by 46', and indicates the intensity of the reflection of blue light. A further value is ascertained by dividing the cube 30 into six domains 34-39, and corresponds to the ratio of the lengths of the vector 25 and of the cube edge 52. It is therefore denoted by 25', and indicates the intensity of the reflection of turquoise-coloured light. Both values are therefore entered in different domains 53, 54 in FIG. 9, but ultimately relate to the same impurity. This shows the different evaluation that can be effected by the selection of domains 31-39.

It is furthermore to be noted that end-points 7, 29 of total vectors 6, 28, which are located close to the diagonals 12, 40, may randomly come into the one or the other domain. That is to say, it takes only small variations of the measured values to cause the end-points 7, 29 to move from one domain into another domain. In FIG. 9, this could also displace the classification of an impurity into another domain. For this reason, one can also define a grey domain in the vicinity of such diagonals 12, 40 so that, in the cases in which the end-points 7, 29 are located in the grey domain, this can also be output as a result and taken into consideration. This would then require FIG. 2 or 9 to be complemented by a grey domain such as that in FIG. 1 or 3.

When the procedures described above are performed for a plurality of properties, each impurity is classified on the basis of a single property. When an inspection material is inspected in order to find contained impurities or foreign bodies, it can be assumed that, viewed over a greater length of the inspection material, a plurality of properties are measured in such a way that they result in a classification. For this reason, for example, three domains 53, 54 and 55 are provided in FIG. 9, in which values for deviations of respectively one property, and their lengths as known from FIG. 2 for a single property, can be entered. The impurities are thereby clearly classified in respect of a plurality of properties.

Instead of the capability to reflect light of a certain colour, an inspection material containing impurities may also have other properties that could be used for classifying the impurities. Such a property would be, for example, the capability to influence the capacitance of an electrical measuring field of a given frequency. Thus, as shown in FIG. 9, values for the length could be entered, as known, along the axis 14, and capacitance changes at a first frequency $f_1$ entered along the axis or scale 15a, and values at a second frequency $f_2$ entered along the axis or scale 15b. A point 59, 60 shown in this FIG. 9 would then indicate, for example, the extent of influence on the measuring field having the first frequency and on the measuring field having the second frequency, this again being after elimination of the influence of the one frequency according to an appropriate rule. In this case, the domains 54 and 55 would then no longer be assigned to a colour, but to a frequency in an electrical field.

In summary, therefore, the classification, according to the invention, of impurities in longitudinally moving textile inspection material can be achieved through the following procedure steps:

Measurement of a plurality of properties on the inspection material, and output of corresponding measurement values which indicate deviations of the properties from standard values or average values.

Elimination of measurement values except for that of a single property, on the basis of rules that are predefined for this purpose.

Representation of the measurement values of the remaining property together with values for the length in the inspection material for which this remaining property has been measured.

The more properties that are to be measured, the more extensive are rules that are to be applied for eliminating the values of all properties except for one. The classification is to be represented graphically in a coordinate system in which results for a plurality of different properties are to be entered, over a common axis, for the lengths over which these results apply.

The invention claimed is:

1. Procedure for detecting and classifying impurities in longitudinally moving inspection material of textile fibers, comprising the following steps, for at least two properties that are influenced by impurities, measuring values for deviations of these properties from a respective standard value and storing said values in memory, eliminating the values for the deviations according to a predefined rule except for values of one property, ascertaining a value for the deviation, resulting from values of the remaining property, and a value for the length of the deviation on the inspection material, and classifying the impurity according to said deviation and length values.

2. Procedure according to claim 1, wherein, for three properties, values for deviations are ascertained and stored in memory, and values for two properties are eliminated.

3. Procedure according to claim 1, wherein a combined value is first ascertained from the values for the deviations of the properties, and further including the steps of predefining, for the combined value, domains in which such values can be located, and determining values of which property are to be eliminated on the basis of a domain in which the combined value is located.

4. Procedure according to claim 1, wherein the deviations are conceived as vectors, a total vector is obtained, as a combined value, from the deviations, and domains are predefined for the end-point of the total vector in the space.

5. Procedure according to claim 1, wherein, in order to measure values for the properties, the inspection material is illuminated with light having a plurality of colours, the reflection of the light is measured separately for each colour, and measured values are compared with standard values and stored in memory as deviations, and further wherein the deviations are conceived as vectors in a space, a total vector is obtained, as a combined value, from the deviations, domains are predefined for the end-point of the total vector in the space, depending on the domain in which the end-point is located, at least one first vector is eliminated, and from the value of a remaining vector, an intensity is ascertained which is classified together with the value for the length of the deviation on the inspection material.

6. Procedure according to claim 1, wherein the deviations are ascertained with the use of threshold values.

7. Procedure according to claim 1, wherein the impurities are classified in a coordinate system which has an axis for values of the length of the deviation and an axis for values for the magnitude of the deviation.

8. Procedure according to claim 1, wherein at least one axis is divided into a plurality of sections for values for different properties.

* * * * *